United States Patent
Goldau

[19]

[11] Patent Number: 6,077,443

[45] Date of Patent: Jun. 20, 2000

[54] METHOD AND DEVICE FOR MONITORING A VASCULAR ACCESS DURING A DIALYSIS TREATMENT

[75] Inventor: Rainer Goldau, Werneck, Germany

[73] Assignee: Fresenius Medical Care Deutschland GmbH, Germany

[21] Appl. No.: 09/129,646

[22] Filed: Aug. 5, 1998

[30] Foreign Application Priority Data

Aug. 6, 1997 [DE] Germany ............................ 197 34 002

[51] Int. Cl.⁷ ........................... B01D 61/28; B01D 61/30; B01D 61/32; B01D 65/10

[52] U.S. Cl. ............................... 210/741; 210/85; 210/90; 210/97; 210/143; 210/321.65; 210/645; 210/646; 210/739

[58] Field of Search ..................................... 210/645, 646, 210/739, 741, 85, 90, 97, 143, 416.1, 321.65

[56] References Cited

U.S. PATENT DOCUMENTS 4,501,583  2/1985  Troutner ..................................... 210/90

FOREIGN PATENT DOCUMENTS

| 0 328 163 | 4/1984 | European Pat. Off. . |
|---|---|---|
| 611 228 | 8/1984 | European Pat. Off. . |
| 332 330 | 9/1989 | European Pat. Off. . |
| 0 328 162 | 2/1993 | European Pat. Off. . |
| 28 38 414 | 10/1984 | Germany . |
| 42 39 937 | 6/1994 | Germany . |
| WO 97 10013 | 3/1997 | WIPO . |

*Primary Examiner*—John Kim
*Attorney, Agent, or Firm*—Kenyon & Kenyon

[57] ABSTRACT

In a method and device for monitoring a vascular access during a dialysis treatment, pressure pulses generated by a balancing device connected in a dialysis fluid inlet line and drain line are monitored in the extracorporeal blood circulation path. The pressure pulses are detected with a pressure sensor in the venous blood line and are analyzed in an analyzer unit. When there is a characteristic change in pressure pulses in the extracorporeal blood circulation path, a faulty venous access is deduced, i.e., the needle has slipped out. Upon a faulty venous access condition, an alarm generator generates an acoustic and/or optical alarm, and the blood flow in the extracorporeal circulation is interrupted.

14 Claims, 2 Drawing Sheets

METHOD AND DEVICE FOR MONITORING A VASCULAR ACCESS DURING A DIALYSIS TREATMENT

FIELD OF THE INVENTION

The present invention concerns a method and device for monitoring a vascular access during a dialysis treatment.

BACKGROUND OF THE INVENTION

In a hemodiafiltration, or dialysis treatment, system, to remove substances that are eliminated with urine, a patient's blood is sent in an extracorporeal circulation system through a chamber of a dialyzer subdivided into two chambers by a semipermeable membrane, while a dialysis fluid flows through the other chamber. Frequently an arteriovenous fistula is created for access to the vascular system, but it is also possible to insert an implant.

Blood is taken from the patient through an arterial needle which is connected to the arterial blood line of the extracorporeal circulation and is supplied to the patient again through a venous needle connected to the venous blood line.

German Patent Application No. 2,838,414 describes a dialysis machine having a volumetric balancing device. The balancing device consists of two chambers subdivided by a displaceable element, with each chamber having an inlet line for fresh dialysis fluid and a drain line connected to an outlet for spent dialysis fluid. Cutoff valves which are driven and switched by a control unit are arranged in the inlet and drain lines. A pump is arranged in the dialysis fluid path between the dialyzer and the balancing device for conveying the spent dialysis fluid.

For the safety of the patient during the dialysis treatment, monitoring of the vascular access is of crucial importance. Thus, if the venous needle slips out and this error is not detected immediately, it involves great blood loss for the patient.

Protective systems for monitoring a vascular access are known from the area of infusion technology. European Patent Application No. 328,163 describes an infusion apparatus with a pressure transducer in the infusion line for detecting the patient's heart beats in the infusion line if the needle has access to the vascular system. Thus, a faulty vascular access is detected by the fact that the heart beats are no longer measured as pressure pulses in the infusion line.

European Patent Application No. 328,162 describes an infusion apparatus where the pressure pulses generated by the infusion pump in the infusion line are monitored. If a needle slips out, it is detected by a change in shape of the pressure pulses.

A previous dialysis machine with a device for monitoring a vascular access has a pressure transducer arranged in the venous blood line. The pressure transducer detects a pressure drop that occurs when the needle slips out. A study of venous pressure monitoring with dialysis equipment has shown, however, that monitoring of venous return pressure as a protective system to prevent blood loss into the environment can fail when the needle slips out.

International Patent Application No. WO 97/10013 describes a dialysis machine with a monitoring system which monitors in the venous blood line the pressure pulses generated by the blood pump in the arterial blood line. This protective system has the disadvantages that the pressure pulses are generated in the extracorporeal blood circulation. Appropriate equipment needs to be provided on the blood side for this purpose.

SUMMARY OF THE INVENTION

An object of the present invention is to provide a method of monitoring a vascular access during a dialysis treatment. The method permits detection of a faulty vascular access with a high reliability without requiring extensive changes in the dialysis machine.

The present invention therefore provides a method of monitoring a vascular access during a dialysis treatment, in which the blood flows through an arterial blood line of an extracorporeal blood circulation into the blood chamber of a dialyzer which is subdivided by a semipermeable membrane into a blood chamber and a dialysis fluid chamber. The blood is returned from the blood chamber through a venous blood line of the extracorporeal blood circulation. Fresh dialysis fluid is sent over a dialysis fluid inlet line of a dialysis fluid branch to the dialysis fluid chamber of the dialyzer, and spent dialysis fluid is removed from the dialyzer over a dialysis fluid drain line. The pressure of the blood in the extracorporeal blood circulation is monitored, and when a characteristic change in blood pressure is detected, a faulty vascular access is deduced. The method is characterized in that pressure pulses generated in the dialysis fluid path are monitored in the extracorporeal blood circulation, and when a characteristic change in pressure pulses is detected in the extracorporeal blood circulation, a faulty vascular access is deduced.

Another object of the present invention is to provide a machine for dialysis treatment with a device for monitoring a vascular access. The machine recognizes a faulty vascular access with a high reliability and can be implemented with relatively simple technical means.

The present invention therefore provides an apparatus for dialysis treatment having an arterial blood line (5) of an extracorporeal blood circulation which is connected to the inlet of a blood chamber (3) of a dialyzer (1) that is subdivided by a semipermeable membrane (2) into the blood chamber (13) and a dialysis fluid chamber (4). The extracorporeal blood circulation has a venous blood line (7), which is connected to the outlet of the blood chamber. Also provided is a dialysis fluid inlet line (10) of a dialysis fluid path, which is connected to the inlet of the dialysis fluid chamber, and a dialysis fluid outlet line (11), which is connected to the outlet of the dialysis fluid chamber. A device (25) for monitoring a vascular access during the dialysis treatment has a pressure sensor (26) to monitor the pressure of the blood in the extracorporeal circulation, and an analyzer unit (27) which monitors the pressure signal of the pressure sensor and infers a faulty vascular access when there is a characteristic change in the pressure signal. The apparatus is characterized in that a pressure pulse generator (13) is provided in the dialysis fluid path (10, 11) to generate pressure pulses, and that the analyzer unit (27) monitors, in the extracorporeal circulation, the pressure pulses generated in the dialysis fluid path, concluding that the vascular access is faulty when there is a characteristic change in the pressure pulses in the extracorporeal circulation. The pressure pulse generator 13 advantageously can be a dialysis fluid balancing device.

With the method according to the present invention, stimulation of pressure pulses in the extracorporeal circulation path is not necessary. To this extent, the method can be implemented with known dialysis equipment using existing facilities. The pressure pulses are not generated on the blood side of the dialyzer but instead on the dialysate side. The pressure pulses generated in the dialysis fluid path are then monitored in the extracorporeal circulation path, and when there is a characteristic change in the pressure pulses in the extracorporeal circulation path, it is concluded that the vascular access is faulty, i.e., that the needle has slipped out.

Surprisingly, pressure pulses generated on the dialysate side also are able to be detected on the blood side. Such pressure pulses can be generated in principle by any valve or pump arranged on the dialysate side. Thus, the pressure pulses generated on the dialysate side in switching the balancing chambers of the balancing device can also be detected on the blood side. For (negative) pressure stimulation, the method according to the present invention advantageously makes use of the balancing device, present in the dialysis machines anyway, which is set up for balancing fresh and spent dialysis fluid in the dialysis fluid path. Thus, generating pressure in the extracorporeal circulation is no longer necessary. The pressure pulses generated by the balancing device can be monitored in the arterial or venous blood lines using pressure sensors which are present anyway in the dialysis machines. As an alternative, to generate pressure pulses, it is also possible to use the ultrafiltration pump, the substituate pump or other valves which are provided in the dialysis fluid path either upstream or downstream of the dialysis fluid chamber of the dialyzer.

The pressure pulses may even be measured in the arterial blood line upstream of the arterial blood pump. However, pressure pulse monitoring is expediently performed in the venous blood line to detect the fact that the venous needle has slipped out.

Pressure pulses are generated by the balancing device when the balancing chamber halves are switched by the control of the cutoff elements arranged in the inlet and outlet lines to and from the balancing chamber. Since the control times of the valves are known, the pressure pulses generated by the balancing device can be simply filtered out of other asynchronous signals.

If the needle slips out, this is detected by a change in the characteristic property of the pressure pulses monitored in the extracorporeal circulation path. When the needle slips out, the pressure pulses show pronounced transient characteristics which can be attributed to reflection of the pressure waves at the then "free end" of the blood line. The slipping out of the needle is advantageously detected in that the periodic pressure curve is measured in the extracorporeal circulation path with proper vascular access, i.e., with the needle in place, at the start of the dialysis treatment, and the results are deposited in a memory. During the dialysis treatment, the pressure characteristic in the extracorporeal circulation path is measured continuously and compared with the stored pressure characteristic for monitoring of the transient characteristics. When there is a certain signal deviation, which can be attributed to the occurrence of the transient characteristic, it is concluded that the vascular access is faulty. However, it is also possible to determine the signal deviation between the maximum which occurs after each pressure pulse and the minimum following the maximum and to compare it with a predetermined threshold value, with a faulty vascular access being deduced when the signal deviation is greater than the threshold value.

An alarm is preferably triggered when the vascular access is faulty. In addition, blood flow in the extracorporeal circulation is interrupted to prevent blood loss.

The method according to the present invention, which is based on measuring, in the extracorporeal blood circulation path, pressure pulses generated in the dialysis fluid path, can also be combined with other methods of detecting a faulty vascular access, e.g., monitoring a pressure drop in the extracorporeal circulation path. This further increases the reliability of the monitoring system.

BRIEF DESCRIPTION OF THE DRAWINGS

An embodiment of the present invention is presented below with reference to the drawings, in which.

DETAILED DESCRIPTION OF THE PREFERRED EMBODIMENTS

Figure 1:
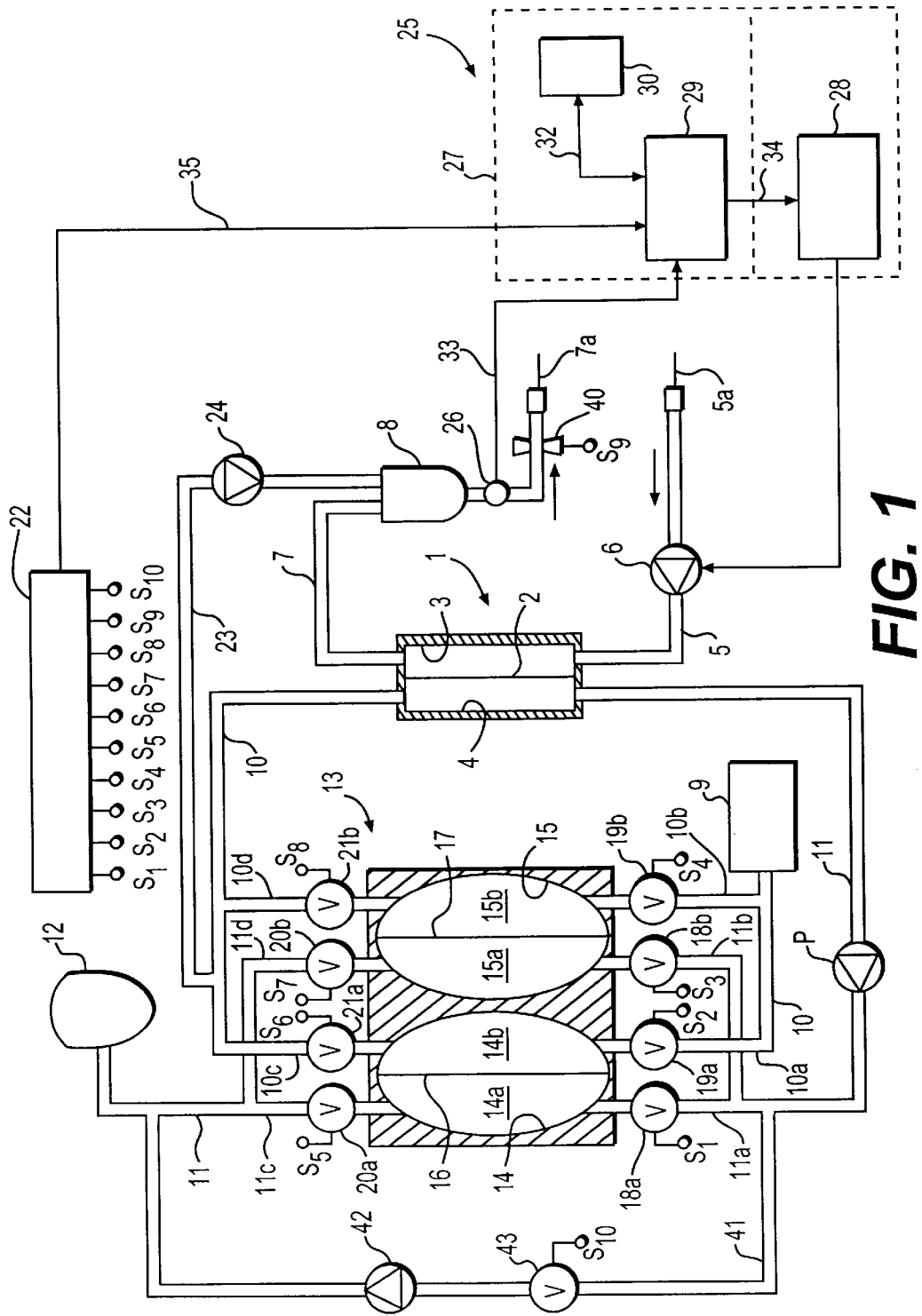
FIG. 1 shows a simplified schematic diagram of a preferred embodiment of a hemodiafiltration system with a device for monitoring a vascular access.

FIG. 1 shows a preferred embodiment of a hemodiafiltration system in a simplified schematic diagram. The hemodiafiltration system has a dialyzer 1 which is subdivided by a semipermeable membrane 2 into a blood chamber 3 and a dialysis fluid chamber 4. An arterial blood line 5 is connected to the inlet of the blood chamber 3, with a connecting blood pump 6. Downstream from blood chamber 3, a venous blood line 7 leads from the outlet of the blood chamber to the patient. A drip chamber 8 is connected to venous blood line 7. Needles 5a and 7a which are inserted into the arterial and venous parts of the patient's fistula are connected at the ends of arterial and venous blood lines 5 and 7. A venous hose clamp 40 which is electromagnetically operable is connected to venous blood line 7.

Fresh dialysis fluid is supplied in a dialysis fluid source 9. A dialysis fluid inlet line 10 leads from dialysis fluid source 9 to the inlet of the dialysis fluid chamber 4 of dialyzer 1, while a dialysis fluid drain line 11 leads from the outlet of the dialysis fluid chamber to a drain 12. For balancing the dialysis fluid, a balancing device 13 is connected to the dialysis fluid inlet and drain lines 10 and 11, respectively. A dialysis fluid pump P is connected to dialysis fluid drain line 11 downstream from dialyzer 4.

Balancing device 13 has two balancing chambers 14 and 15, each having the same volume, subdivided by movable partitions 16 and 17, respectively, into first balancing chamber halves 14a and 15a, respectively, and second balancing chamber halves 14b and 15b, respectively. Movable partitions 16 and 17 are each, for example, a flexible membrane.

The part of the dialysis liquid inlet line 10 leading to balancing device 13 is divided into two line branches 10a and 10b, with line branch 10a leading to the inlet of second chamber half 14b of first balancing chamber 14, and the other line branch 10b leading to the inlet of second chamber half 15b of the second balancing chamber 15. The part of the dialysis fluid inlet line 10 leading away from balancing device 13 is divided into two line branches 10c and 10d, of which one line branch 10c is connected to the outlet of second chamber half 14b of first balancing chamber 14, and the other line branch 10d connected to the outlet of the second chamber half 15b of the second balancing chamber 15.

The part of the dialysis liquid outlet line 11 leading to balancing device 13 is also divided into two line segments 11a and 11b, with one line segment 11a connected to the inlet of first chamber half 14a of first balancing chamber 14, and the other line segment 11b connected to the inlet of first chamber half 15a of second balancing chamber 15. The outlet of the first chamber half 14a of first balancing chamber 14 is connected to drain 12 over line branch 11c, and the outlet of the first chamber half 15a of the second balancing chamber 15 is connected to outlet 12 over line branch 11d of dialysis fluid drain line 11. Cutoff elements in the form of electromagnetically operable valves 18a, 18b, 19a, 19b, 20a, 20b, 21a and 21b are provided in the individual line branches 10a through 10d and 11a through 11d, and are connected to a central control unit 22 by control lines $S_1$ through $S_8$. Venous hose clamp 40 is connected by control line $S_9$ to control unit 22 for operation thereof.

Downstream from the balancing device, a substitute inlet line 23 branches off from dialysis fluid inlet line 10, a substitute pump 24 being connected to this substitute inlet line. Substitute inlet line 23 leads into drip chamber 8 arranged in the venous blood line (post-dilution). As an alternative, the substituate inlet line may also be connected to a drip chamber arranged upstream from the dialyzer (pre-dilution).

Downstream from dialysis fluid pump P, ultrafiltration line 41 branches off from the dialysis fluid drain line, to which ultrafiltration line an ultrafiltration pump 42 is connected to remove ultrafiltrate. Ultrafiltration line 41 leads to drain 12. Upstream from ultrafiltration pump 42, a valve 43 is arranged in ultrafiltration line 41 to permit interruption of the ultrafiltration line. Valve 43 is driven by control unit 22 over control line $S_{10}$.

The hemodiafiltration system functions as follows:

In a first balancing cycle, valves 18a, 19b, 21a and 20b are opened by central control unit 22, with all the other valves being closed.

Fresh dialysis fluid flows out of dialysis fluid source 9 into the second chamber half 15b of the second balancing chamber 15, so that spent dialysis fluid sent into the first chamber half 15a in a preceding cycle is discharged into drain 12. At the same time, spent dialysis fluid is pumped by dialysis fluid pump P out of dialysis fluid chamber 4 of dialyzer 1 into the first chamber half 14a of first balancing chamber 14, so that fresh dialysis fluid previously sent to second chamber half 14b is discharged from the second chamber half and sent to dialysis fluid chamber 4.

In a second balancing cycle, valves 18b, 19a, 20a and 21b are opened, with all the other valves being closed. Fresh dialysis fluid flows into the second chamber half 14b of the first balancing chamber 14 of balancing device 13, so that spent dialysis fluid from the first chamber half 14a is discharged into the drain. At the same time, spent dialysis fluid is pumped into first chamber half 15a of second balancing chamber 15, so that fresh dialysis fluid from the second chamber half 15b is discharged and sent to dialysis fluid chamber 4.

Fluid is removed from the closed system with ultrafiltration pump 42 turned on.

The hemodiafiltration system has a device 25 for monitoring the vascular access, i.e., proper seating of the needle. Monitoring device 25 comprises a pressure sensor 26 arranged in venous blood line 7, an analyzer unit 27 and an alarm generator 28.

Negative pressure pulses generated by balancing device 13 in switching valves 18 through 21 in dialysis fluid inlet and drain lines 10 and 11 can be measured with pressure sensor 26 in venous blood line 7. The pressure pulse generator of the present invention thus in this embodiment of the present invention advantageously is comprised of the balancing device 13.

Figure 2:
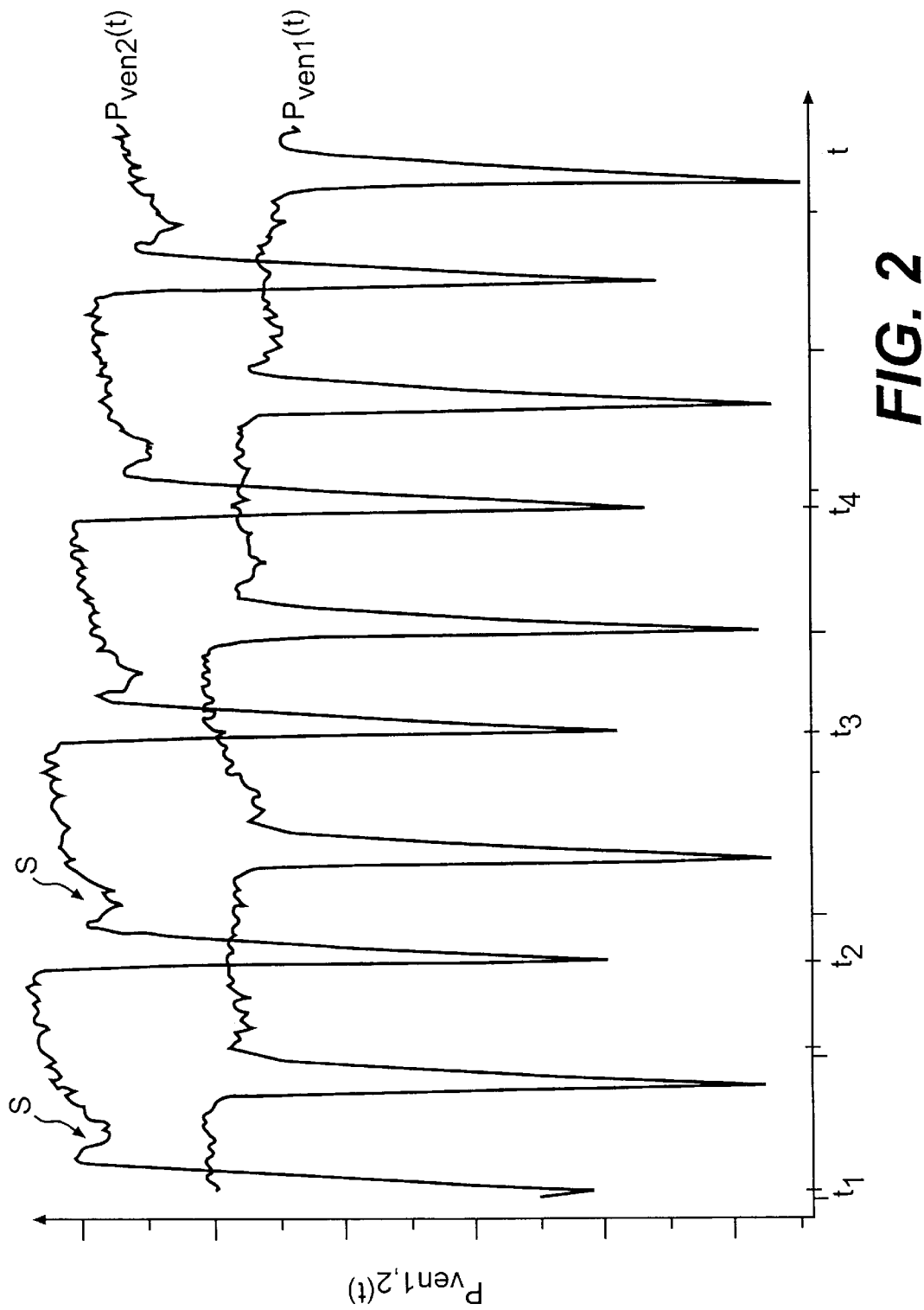
FIG. 2 shows the blood pressure as a function of time in the venous blood line with the needle inserted and with the needle removed.

FIG. 2 shows a plot of the pressure signal generated by pressure sensor 26 with the needle inserted ($P_{ven1}(t)$) and after the needle has slipped out ($P_{ven2}(t)$). The pressure in venous blood line 7 drops sharply at switching times $t_1$, $t_2$, etc., of valves 18 through 21 of balancing device 13. When venous needle 7a has slipped out, there is a marked oscillation S after switching the valves. This property of pressure pulses in the extracorporeal circulation path, which is characteristic of a faulty vascular access, is detected by analyzer unit 27.

Analyzer unit 27 has a central processor 29 and a memory 30 which communicates with central processor 29 over a data line 32. The analyzer unit is connected by a signal line 33 to the signal output of pressure sensor 26 and by a signal line 34 to an alarm generator 28. In addition, the analyzer unit receives control signals from the valves of control unit 22 over data line 35.

The periodic pressure characteristic in venous blood line 7 with proper vascular access, i.e., with the needle inserted, is stored in memory 30 of analyzer unit 27. This pressure characteristic may vary from one patient to the next and may also vary as a function of the hose system used and the respective dialyzer. Therefore, the pressure characteristic is measured with pressure sensor 26 in venous blood line 7 at the start of the dialysis treatment when there is proper vascular access and is stored in memory 30 (calibration).

During the dialysis treatment, the pressure characteristic measured with pressure sensor 26 in the central processor 29 is compared continuously with the stored pressure characteristic which is read out of memory 30. This comparison can be performed in central processor 29 on the basis of known statistical methods to detect a signal deviation on the basis of the oscillation S which can be attributed to the needle slipping out. Thus, for example, the averaged pressure characteristics can be compared, and if the value is below a certain standard deviation, this is recognized as a faulty vascular access, i.e., slippage of the needle. When the pressure signal property that is characteristic of faulty vascular access is detected, the analyzer unit produces an alarm signal that is received by alarm generator 28. Alarm generator 28 gives an acoustic and/or optical alarm and generates a control signal for blood pump 6 arranged in arterial blood line 5. When blood pump 6 receives the control signal, the blood flow is interrupted automatically, so that blood loss cannot occur when the needle slips out. In addition, venous clamp 40 is operated. The boloood pump 6 thus comprises an interruptor for the blood flow.

To detect a faulty vascular access, the pressure pulses generated by ultrafiltration pump 42 or substituate pump 24 in the extracorporeal circulation path can also be monitored.

What is claimed is:

1. A method of monitoring a vascular access during a dialysis treatment using a dialyzer subdivided into a blood chamber by a semipermeable membrane into a blood chamber and a dialysis fluid chamber, the method comprising:

passing blood through an arterial blood line of an extracorporeal blood circulation path into the blood chamber and returning the blood from the blood chamber through a venous blood line of the extracorporeal blood circulation path;

providing fresh dialysis fluid via a dialysis fluid inlet line of a dialysis fluid path to the dialysis fluid chamber and removing spent dialysis fluid from the dialyzer via a dialysis fluid drain line of the dialysis fluid path;

generating first pressure pulses in the dialysis fluid path during operation of the dialyzer; and monitoring a waveform of second pressure pulses in the extracorporeal blood circulation path, induced by the first pressure pulses generated in the dialysis fluid path so that a faulty vascular access is deduced when a characteristic change in the second pressure pulses waveform is detected.

2. The method as recited in claim 1 wherein the second pressure pulses monitored in the extracorporeal blood circulation path are generated by a balancing device connected in the dialysis fluid inlet line and dialysis fluid drain line, the balancing device having at least one balancing chamber subdivided by a movable partition into two balancing chamber halves, one balancing chamber half being filled with fresh dialysis fluid and the other balancing chamber half having spent dialysis fluid discharged in a first balancing cycle, one half of the balancing chamber being filled with spent dialysis fluid and the other half of the balancing chamber having fresh dialysis fluid discharged and in a second balancing cycle.

3. The method as recited in claim 1 further comprising measuring a correct vascular access pressure in the extracorporeal blood circulation path and storing a corresponding periodic pressure characteristic signal at the start of a dialysis treatment, and wherein the monitoring step includes continuously measuring the pressure during the dialysis treatment and comparing a resulting signal with the stored periodic pressure characteristic signal, the faulty vascular access being deduced from the comparing.

4. The method as recited in claim 1 wherein the pressure in the extracorporeal blood circulation path is monitored in the venous blood line.

5. The method as recited in claim 1 wherein the pressure in the extracorporeal blood circulation path is monitored in the arterial blood line.

6. The method as recited claim 1 further comprising triggering an alarm when the faulty vascular access is deduced.

7. The method as recited in claim 1 further comprising interrupting blood flow in the extracorporeal blood circulation path when faulty vascular access is deduced.

8. An apparatus for dialysis treatment comprising:

a dialyzer subdivided by a semipermeable membrane into a blood chamber and a dialysis fluid chamber;

an extracorporeal blood circulation path including an arterial blood line and a venous blood line, the arterial blood line being connected to an inlet of a blood chamber, the venous blood line being connected to an outlet of the blood chamber;

a dialysis fluid path having a dialysis fluid inlet line and a dialysis fluid outlet line, the dialysis fluid inlet line being connected to an inlet of the dialysis fluid chamber, the dialysis fluid outlet line being connected to an outlet of the dialysis fluid chamber;

a pressure pulse generator disposed in the dialysis fluid path for generating first pressure pulses during operation of the dialyzer; and a device for monitoring a vascular access during the dialysis treatment, the device including a pressure sensor and an analyzer unit, the pressure sensor for monitoring a pressure of the blood in the extracorporeal blood circulation path so as to be able to sense second pressure pulses induced by the first pressure pulses and for producing a corresponding signal, and the analyzer unit for monitoring the corresponding signal and for determining that the vascular access is faulty upon a characteristic change in second pressure pulses waveform.

9. The apparatus as recited in claim 8 wherein the pressure pulse generator includes a balancing device connected in the dialysis fluid inlet line and the dialysis fluid drain line for balancing fresh and spent dialysis fluid, the balancing device having at least one balancing chamber subdivided by a movable partition into two balancing chamber halves having chamber inlet and drain lines and having cutoff elements disposed in the chamber inlet and drain lines.

10. The apparatus as recited in claim 8, wherein the analyzer unit includes a memory for storing a pressure pulse characteristic signal of a proper vascular access and a central processor for comparing the second pressure pulses waveform with the pressure pulse characteristic signal, and for detecting a faulty vascular access upon a certain signal deviation.

11. The apparatus as recited in claim 8 wherein the pressure sensor is disposed in the venous blood line.

12. The apparatus as recited in claim 8 wherein the pressure sensor is disposed in the arterial blood line.

13. The apparatus as recited in claim 8 further comprising an alarm generator for generating an alarm when the faulty vascular access is deduced.

14. The apparatus as recited in claim 8 further comprising an interrupter for interrupting blood flow in the extracorporeal circulation path when the analyzer unit detects the faulty vascular access.

* * * * *

(12) EX PARTE REEXAMINATION CERTIFICATE (7093rd)
United States Patent
Goldau

(10) Number: US 6,077,443 C1
(45) Certificate Issued: Oct. 6, 2009

(54) METHOD AND DEVICE FOR MONITORING A VASCULAR ACCESS DURING A DIALYSIS TREATMENT

(75) Inventor: Rainer Goldau, Werneck (DE)

(73) Assignee: Fresenius Medical Care Deutschland GmbH, Bad Homburg (DE)

Reexamination Request:
No. 90/010,239, Aug. 8, 2008

Reexamination Certificate for:
Patent No.: 6,077,443
Issued: Jun. 20, 2000
Appl. No.: 09/129,646
Filed: Aug. 5, 1998

(51) Int. Cl.
*A61M 1/16* (2006.01)
*A61M 1/36* (2006.01)
*A61M 5/168* (2006.01)

(52) U.S. Cl. .................. 210/741; 210/143; 210/645; 210/646; 210/321.65; 210/739; 210/90; 210/97; 210/85

(58) Field of Classification Search .................. None
See application file for complete search history.

(56) References Cited

U.S. PATENT DOCUMENTS

| 4,710,163 A | 12/1987 | Butterfield |
| 5,516,429 A | 5/1996 | Snodgrass et al. |
| 5,591,344 A | 1/1997 | Kenley et al. |
| 6,090,048 A | 7/2000 | Hertz et al. |

*Primary Examiner*—Krisanne Jastrzab

(57) ABSTRACT

In a method and device for monitoring a vascular access during a dialysis treatment, pressure pulses generated by a balancing device connected in a dialysis fluid inlet line and drain line are monitored in the extracorporeal blood circulation path. The pressure pulses are detected with a pressure sensor in the venous blood line and are analyzed in an analyzer unit. When there is a characteristic change in pressure pulses in the extracorporeal blood circulation path, a faulty venous access is deduced, i.e., the needle has slipped out. Upon a faulty venous access condition, an alarm generator generates an acoustic and/or optical alarm, and the blood flow in the extracorporeal circulation is interrupted.

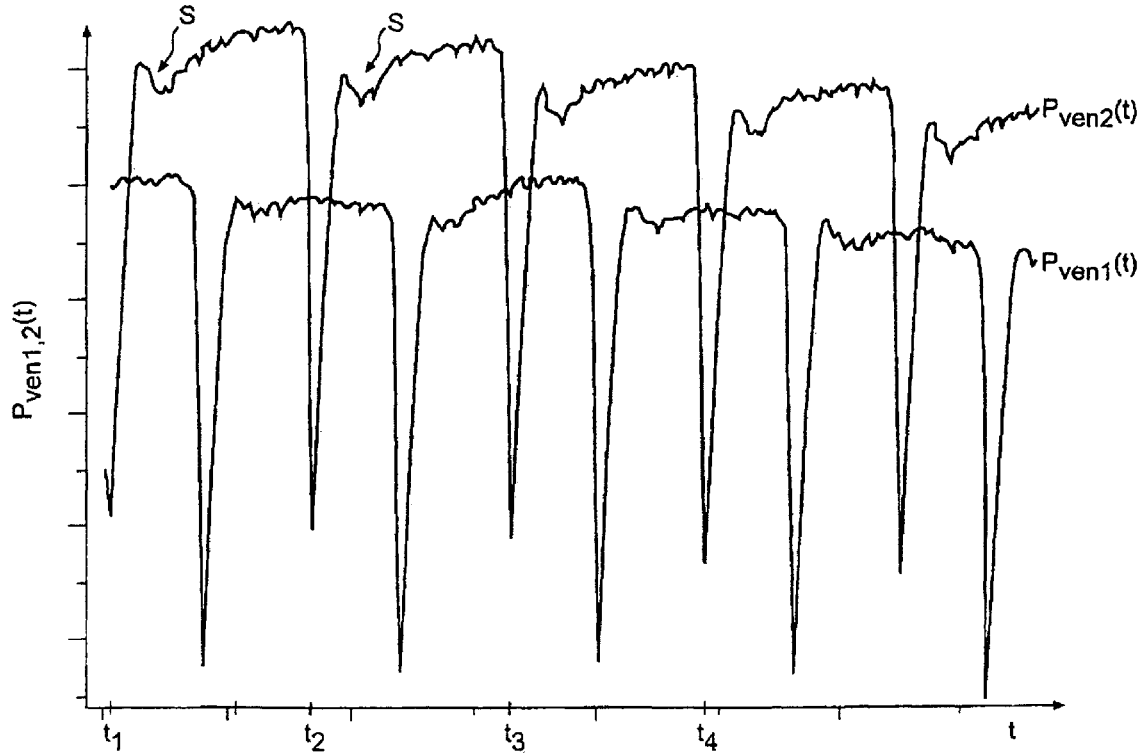

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

* * * * *